(12) United States Patent
Kurochi et al.

(10) Patent No.: US 8,891,727 B2
(45) Date of Patent: Nov. 18, 2014

(54) RADIATION IMAGING APPARATUS, RADIATION DETECTING APPARATUS AND RADIATION FOCAL-POINT MOVEMENT DETECTING METHOD

(75) Inventors: Haruo Kurochi, Tokyo (JP); Abdelaziz Ikhlef, Waukesha, WI (US); Joseph James Lacey, Waukesha, WI (US); Mark Adamak, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 474 days.

(21) Appl. No.: 13/404,537

(22) Filed: Feb. 24, 2012

(65) Prior Publication Data

US 2013/0223588 A1   Aug. 29, 2013

(51) Int. Cl.
*H05G 1/02* (2006.01)
*G21K 1/02* (2006.01)
*G21K 1/10* (2006.01)

(52) U.S. Cl.
USPC ............................................ 378/19; 378/149

(58) Field of Classification Search
USPC ............... 378/4–20, 145, 147, 149, 204, 210;
250/370.01, 370.08, 370.09, 396 R,
250/397, 505.1, 526
See application file for complete search history.

(56) References Cited

U.S. PATENT DOCUMENTS

| 7,702,073 B2 | 4/2010 | Harding |
| 7,869,573 B2 | 1/2011 | Banchieri |
| 7,889,845 B2 | 2/2011 | Harding |
| 2009/0168968 A1 | 7/2009 | Banchieri |
| 2010/0014642 A1 | 1/2010 | Halazonetis et al. |
| 2010/0158195 A1 | 6/2010 | Wirth |
| 2010/0239072 A1 | 9/2010 | Kurochi |

FOREIGN PATENT DOCUMENTS

JP   2010005015   1/2010

*Primary Examiner* — Anastasia Midkiff
(74) *Attorney, Agent, or Firm* — Armstrong Teasdale LLP

(57) ABSTRACT

A radiation imaging apparatus is provided. The radiation imaging apparatus includes a radiation source configured to emit radiation from a first focal point, a plurality of radiation detecting elements disposed opposite to the radiation source and arranged in a channel direction, a plurality of collimator plates provided along the channel direction so as to separate the radiation detecting elements, the collimator plates including radiation absorption members at surfaces of at least one first collimator plate located on a first end side and at least one second collimator plate located on a second end side such that radiation shielding effects of the first and second collimator plates become substantially equivalent when the surfaces of the first and second collimator plates are located along a radial direction from a second focal point, and a data acquisition unit configured to acquire radiation projection data from the radiation detecting elements.

20 Claims, 16 Drawing Sheets

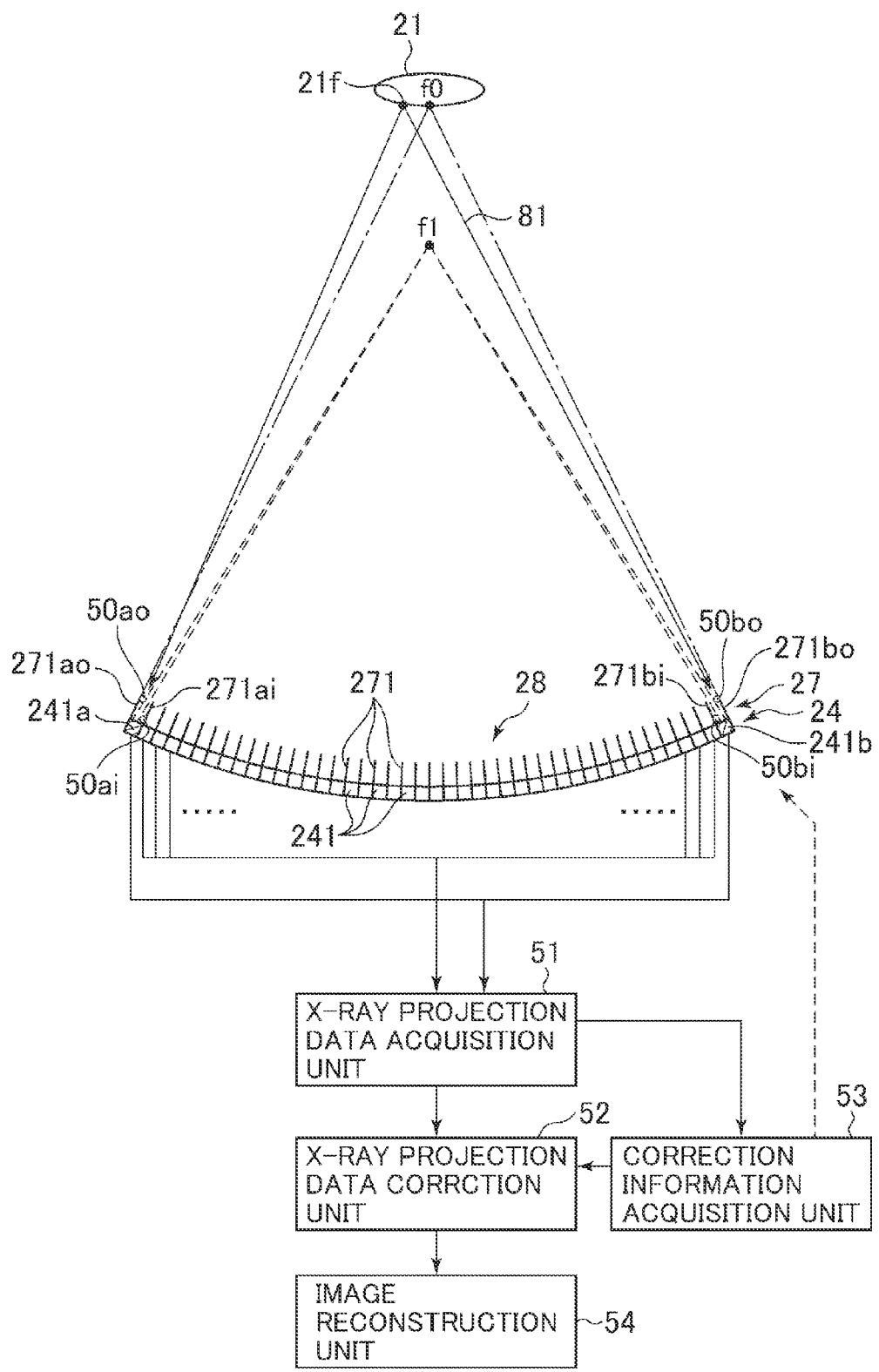

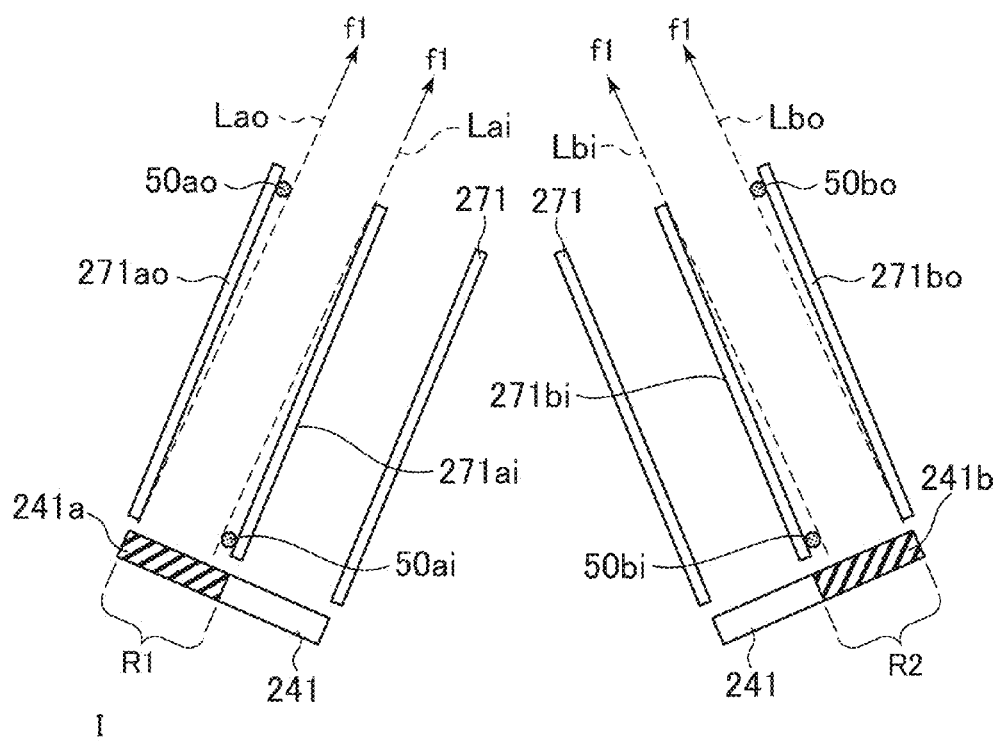
FIG. 4A                    FIG. 4B

RADIATION IMAGING APPARATUS, RADIATION DETECTING APPARATUS AND RADIATION FOCAL-POINT MOVEMENT DETECTING METHOD

BACKGROUND OF THE INVENTION

The present invention relates to radiation imaging and specifically to a technology for suppressing degradation in quality of a reconstructed image due to variations in position of a radiation focal point.

As a representative of a radiation imaging apparatus which performs imaging using radiation, there has been known an X-ray CT (Computed Tomography) apparatus. A data acquisition system of the X-ray CT apparatus is principally includes an X-ray source and an X-ray detection section. The X-ray detection section further includes an X-ray detector and a collimator. The collimator includes a plurality of collimator plates provided so as to separate or partition X-ray detecting elements in the X-ray detector on their detection surface sides. See, for example, FIG. 16 of Japanese Unexamined Patent Publication No. 2010-005015.

The collimator is configured to remove scattered radiation to thereby prevent degradation of an output of each X-ray detecting element due to the scattered radiation and to obtain a distinct reconstructed image. If segments separated by collimator plates are not properly directed to an X-ray source, it may cause degradation of a reconstructed image. Therefore, the collimator plates are generally required to have very high accuracy of their installation.

There is no problem if the collimator plates form the segments in a completely ideal state. However, since the collimator used in the X-ray CT apparatus utilizes about 1000 collimator plates, for example, some small variations may actually occur.

Although the X-ray source that emits X-rays is ideally a point source, it actually has some width and the position thereof slightly changes depending on the environment. When the X-ray source is an X-ray tube, for example, a target of the X-ray tube is slightly deformed depending on a change in its temperature. Hence, the position and size of an X-ray focal point changes.

Due to variations in segments formed by the collimator plates and variations (focal movement) in the position of the X-ray focal point of the X-ray source, variations in segments in X-ray detecting elements are developed at a rate in a region on which X-rays are actually applied, to a region having an ability to receive X-rays by the X-ray detector. The variations direct noise that flows into the X-ray detector and thereby degrades the quality of a reconstructed image. Since the required accuracy is high even if the collimator would be fabricated under a fully managed environment, variations in the X-ray CT apparatus may not satisfy the accuracy required for the reconstructed image.

With such a situation, there has been a demand for a technology for correcting the effects of slight variations in the position of a radiation focal point to radiation projection data.

BRIEF DESCRIPTION OF THE INVENTION

In a first aspect, a radiation imaging apparatus is provided. The radiation imaging apparatus includes a radiation source which emits radiation to a target for imaging from a first focal point corresponding to a radiation focal point, a plurality of radiation detecting elements disposed opposite to the radiation source and arranged in a channel direction, a plurality of collimator plates provided along the channel direction on the detection surface sides of the radiation detecting elements so as to separate the radiation detecting elements in the channel direction respectively, the collimator plates being provided with radiation absorption members at surfaces of at least one first collimator plate located on one end side, of the collimator plates and at least one second collimator plate located on the other end side, of the collimator plates in such a manner that radiation shielding effects of the first and second collimator plates become substantially equivalent to a case where the surfaces of the first and second collimator plates are provided along a radial direction from a second focal point different from the first focal point, and a data acquisition unit for acquiring radiation projection data for image reconstruction from the radiation detecting elements.

In a second aspect, the radiation imaging apparatus according to the first aspect is provided, wherein the radiation absorption members are respectively provided at plate surfaces opposite to each other, of a pair of first collimator plates by which a first radiation detecting element on one end side in the channel direction, of the radiation detecting elements is separated, and plate surfaces opposite to each other, of a pair of second collimator plates by which a second radiation detecting element on the other end side in the channel direction, of the radiation detecting elements is separated, wherein the radiation absorption members provided at the pair of first collimator plates are formed and disposed in such a manner that a direction tangent to an end on the side near the radiation source, of the one first collimator plate of the pair of first collimator plates and the radiation absorption member provided at the one first collimator plate, and a direction tangent to an end on the side distant from the radiation source, of the other first collimator plate thereof and the radiation absorption member provided at the other first collimator plate extend along the radial direction from the second focal point closer to the radiation detecting elements than the first focal point, and wherein the radiation absorption members provided at the pair of second collimator plates are formed and disposed in such a manner that a direction tangent to an end on the side near the radiation source, of the one second collimator plate of the pair of collimator plates and the radiation absorption member provided at the one second collimator plate, and a direction tangent to an end on the side distant from the radiation source, of the other second collimator plate thereof and the radiation absorption member provided at the other second collimator plate extend along the radial direction from the second focal point.

In a third aspect, the radiation imaging apparatus according to the second aspect is provided, further including a correcting unit for correcting the effects of a movement of the first focal point to radiation projection data, based on outputs of the first and second radiation detecting elements.

In a fourth aspect, the radiation imaging apparatus according to the third aspect is provided, wherein the correcting unit corrects the radiation projection data, based on a balance between the outputs of the first and second radiation detecting elements.

In a fifth aspect, the radiation imaging apparatus according to the fourth aspect is provided, wherein the correcting unit corrects the radiation projection data, based on a ratio between the outputs of the first and second radiation detecting elements.

In a sixth aspect, the radiation imaging apparatus according to the fifth aspect is provided, wherein the correcting unit corrects the radiation projection data, based on the relation between the ratio of the outputs of the first and second radiation detecting elements and sensitivities of the respective radiation detecting elements, and the output ratio actually obtained.

In a seventh aspect, the radiation imaging apparatus according to the sixth aspect is provided, further including an acquisition unit for moving the first focal point to a plurality of positions different from one another and detecting radiation emitted from the first focal point by the radiation detecting elements every position to thereby acquire information indicative of the relation.

In an eighth aspect, the radiation imaging apparatus according to any one of the second to seventh aspects is provided, wherein the first and second radiation detecting elements are respectively located at one and other ends along the channel direction, of the radiation detecting elements.

In an eighth aspect, the radiation imaging apparatus according to any one of the second to seventh aspects is provided, wherein the first and second radiation detecting elements are respectively located at one and other ends along the channel direction, of the radiation detecting elements.

In a tenth aspect, the radiation imaging apparatus according to any one of the first to ninth aspects is provided, wherein each of the radiation absorption members is a columnar member with a slice direction as its axial direction.

In an eleventh aspect, the radiation imaging apparatus according to the tenth aspect is provided, wherein the radiation absorption members are formed in such a manner that columnar-axis sections thereof become circular or ellipsoidal.

In a twelfth aspect, the radiation imaging apparatus according to the tenth aspect is provided, wherein the radiation absorption members are formed in such a manner that columnar-axis sections thereof become graphics that change in thickness along the radial direction from the second focal point.

In a thirteenth aspect, a radiation detecting apparatus is provided. The radiation detecting apparatus includes a plurality of radiation detecting elements disposed opposite to a radiation source which emits radiation to a target for imaging from a first focal point corresponding to a radiation focal point and arranged in at least a channel direction, and a plurality of collimator plates provided along the channel direction on the detection surface sides of the radiation detecting elements so as to separate the radiation detecting elements in the channel direction respectively, the collimator plates being provided with radiation absorption members at surfaces of at least one first collimator plate located on one end side, of the collimator plates and at least one second collimator plate located on the other end side, of the collimator plates in such a manner that radiation shielding effects of the first and second collimator plates become substantially equivalent to a case where the surfaces of the first and second collimator plates are provided along a radial direction from a second focal point different from the first focal point.

In a fourteenth aspect, the radiation detecting apparatus according to the thirteenth aspect is provided, wherein the radiation absorption members are respectively provided at plate surfaces opposite to each other, of a pair of first collimator plates by which a first radiation detecting element on one end side in the channel direction, of the radiation detecting elements is separated, and plate surfaces opposite to each other, of a pair of second collimator plates by which a second radiation detecting element on the other end side in the channel direction, of the radiation detecting elements is separated, wherein the radiation absorption members provided at the pair of first collimator plates are formed and disposed in such a manner that a direction tangent to an end on the side near the radiation source, of the one first collimator plate of the pair of first collimator plates and the radiation absorption member provided at the one first collimator plate, and a direction tangent to an end on the side distant from the radiation source, of the other first collimator plate thereof and the radiation absorption member provided at the other first collimator plate extend along the radial direction from the second focal point closer to the radiation detecting elements than the first focal point, and wherein the radiation absorption members provided at the pair of second collimator plates are formed and disposed in such a manner that a direction tangent to an end on the side near the radiation source, of the one second collimator plate of the pair of collimator plates and the radiation absorption member provided at the one second collimator plate, and a direction tangent to an end on the side distant from the radiation source, of the other second collimator plate thereof and the radiation absorption member provided at the other second collimator plate extend along the radial direction from the second focal point.

In a fifteenth aspect, the radiation detecting apparatus according to the fourteenth aspect is provided, wherein the first and second radiation detecting elements are respectively located at one and other ends along the channel direction, of the radiation detecting elements.

In a sixteenth aspect, the radiation detecting apparatus according to the fourteenth aspect is provided, wherein the radiation detecting elements are arranged in the channel and slice directions, and wherein the first and second radiation detecting elements respectively include two or more radiation detecting elements different in position in the slice direction.

In a seventeenth aspect, the radiation detecting apparatus according to any one of the thirteenth to sixteenth aspects is provided, wherein each of the radiation absorption members is a columnar member with a slice direction as its axial direction.

In an eighteenth aspect, the radiation detecting apparatus according to the seventeenth aspect is provided, wherein the radiation absorption members are formed in such a manner that columnar-axis sections thereof become circular or ellipsoidal.

In a nineteenth aspect, the radiation detecting apparatus according to the seventeenth aspect is provided, wherein the radiation absorption members are formed in such a manner that columnar-axis sections thereof become graphics that change in thickness along the radial direction from the predetermined position.

In a twentieth aspect, a radiation focal-point movement detecting method is provided. The method includes providing a radiation source which emits radiation to a target for imaging from a first focal point corresponding to a radiation focal point, providing a plurality of radiation detecting elements disposed opposite to the radiation source and arranged in a channel direction, providing a plurality of collimator plates along the channel direction on the detection surface sides of the radiation detecting elements so as to separate the radiation detecting elements in the channel direction respectively, providing radiation absorption members at surfaces of at least one first collimator plate located on one end side, of the collimator plates and at least one second collimator plate located on the other end side, of the collimator plates in such a manner that radiation shielding effects of the first and second collimator plates become substantially equivalent to a case where the surfaces of the first and second collimator plates are provided along a radial direction from a second focal point different from the first focal point, and detecting a movement of the first focal point, based on outputs of each of the radiation detecting elements separated by the first collimator plates and each of the radiation detecting elements separated by the second collimator plates.

According to the above aspects, predetermined radiation detecting elements located on one end and other end sides in a channel direction are separated in the channel direction by collimator plates provided with radiation absorption members at their plate surfaces as described above. Therefore, in the predetermined radiation detecting element located on one end side in the channel direction, the size of a radiation field of radiation becomes a maximum when a radiation focal point is located on the other end side as viewed in the channel direction, whereas in the predetermined radiation detecting element on the other end side as viewed in the channel direction, the size of a radiation field of radiation becomes a maximum when the radiation focal point is located on one end side as viewed in the channel direction. As a result, the position of the radiation focal point can be determined in high resolution based on the outputs of the predetermined radiation detecting elements on the one end and other end sides, and hence the effects of small variations in the position of the radiation focal point to X-ray projection data can be corrected.

BRIEF DESCRIPTION OF THE DRAWINGS

FIG. 2 is a diagram showing a conceptual diagram of a main part related to an imaging process at the X-ray CT apparatus shown in FIG. 1.

FIGS. 4A and 4B are side enlarged diagrams of the peripheries of first and second X-ray detecting elements.

DETAILED DESCRIPTION OF THE INVENTION

An exemplary embodiment is described herein. Incidentally, the present invention is not limited to or by the exemplary embodiment described herein.

Figure 1:
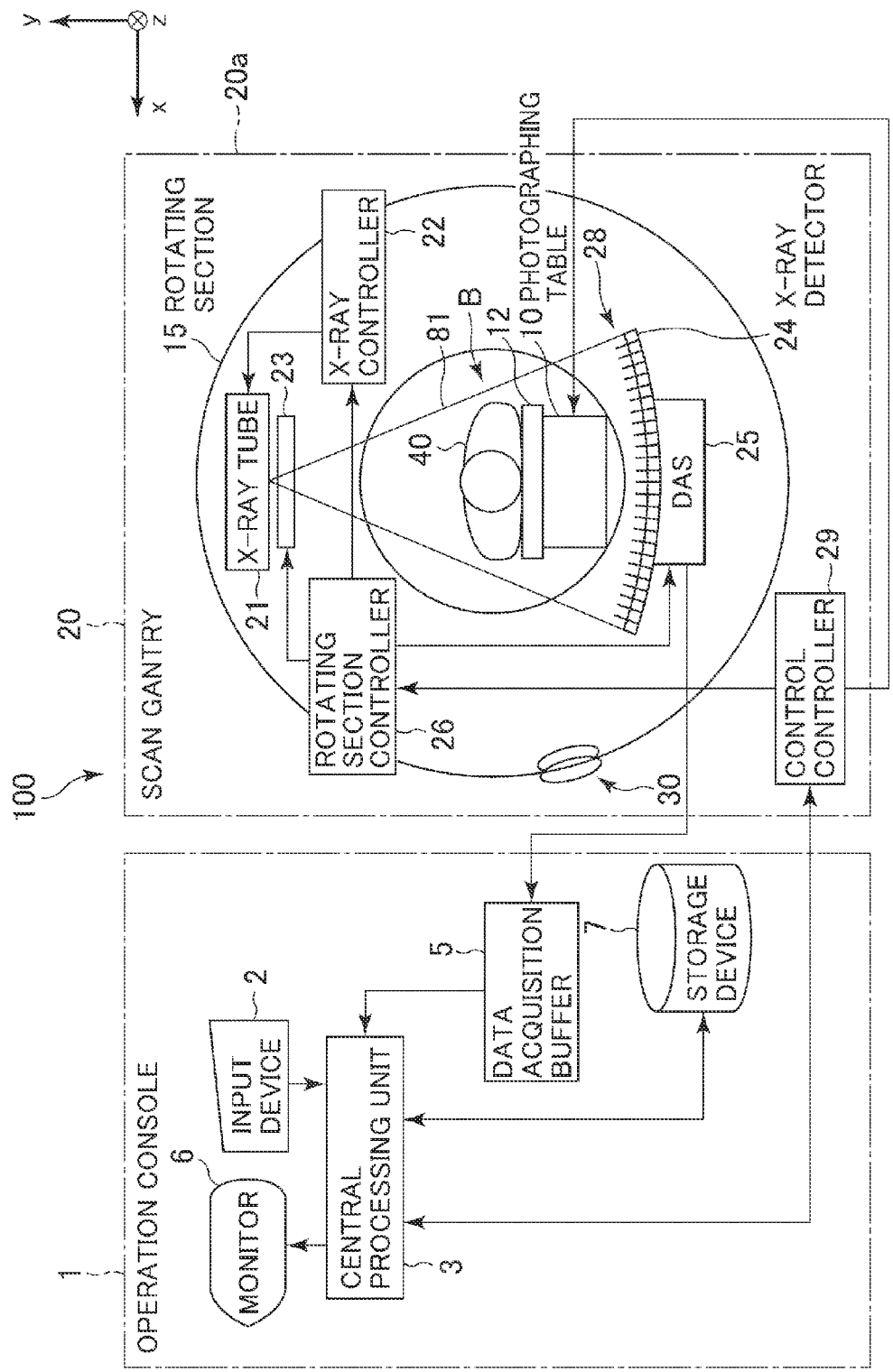
FIG. 1 is a diagram schematically showing a configuration of an exemplary X-ray CT apparatus.

FIG. 1 is a diagram schematically showing a configuration of an exemplary X-ray CT apparatus.

The X-ray CT apparatus 100 is equipped with an operation console 1, a photographing table 10 and a scan gantry 20.

The operation console 1 is equipped with an input device 2 which accepts an input from an operator, a central processing unit 3 which executes control of respective parts for performing subject's imaging, a data process for generating an image, etc., a data acquisition buffer 5 which acquires or collects data acquired by the scan gantry 20, a monitor 6 which displays each image thereon, and a storage device 7 which stores programs, data, etc. therein.

The photographing table 10 is equipped with a cradle 12 which conveys a subject 40 to a cavity portion B of the scan gantry 20 with the subject 40 placed thereon. The cradle 12 is elevated and linearly moved horizontally by a motor built in the photographing table 10. Incidentally, in the exemplary embodiment, the direction of a body axis of the subject 40, i.e., the horizontal linear moving direction of the cradle 12 is assumed to be a z direction, its vertical direction is assumed to be a y direction, and its horizontal direction orthogonal to the z and y directions is assumed to be an x direction.

The scan gantry 20 has a rotating section 15 and a body section 20a which rotatably supports the rotating section 15. The rotating section 15 is provided with an X-ray tube 21, an X-ray controller 22 which controls the X-ray tube 21, an aperture 23 which shapes X-rays 81 generated from the X-ray tube 21 into a fan beam or a cone beam, an X-ray detection section 28 which detects the X-rays 81 penetrated through the subject 40, a DAS (Data Acquisition System)(also called data acquisition apparatus) 25 which converts outputs of the X-ray detection section 28 into X-ray projection data and acquires or collects the same, and a rotating section controller 26 which controls the X-ray controller 22, aperture 23 and DAS 25. The body section 20a is equipped with a control controller 29 which performs communication of control signals or the like with the operation console 1 and the photographing table 10. The rotating section 15 and the body section 20a are electrically coupled to each other via a slip ring 30.

The X-ray tube 21 and the X-ray detection section 28 are disposed opposite to each other with an imaging space in which the subject 40 is placed (i.e., a cavity portion B of the scan gantry 20) interposed therebetween. When the rotating section 15 is rotated, the X-ray tube 21 and the X-ray detection section 28 are rotated about the subject 40 while their positional relationship is maintained. The X-rays 81 shown in the form of the fan beam or cone beam, which are radiated from the X-ray tube 21 and shaped by the aperture 23, penetrate the subject 40 and are applied onto a detection surface of the X-ray detection section 28. The direction of expansion of the X-rays 18 shown in the form of this fan beam or cone beam at an xy plane is called a channel (CH) direction, and the direction of expansion thereof in the z direction or the z direction itself is called a slice (SL) direction.

Figure 3A:
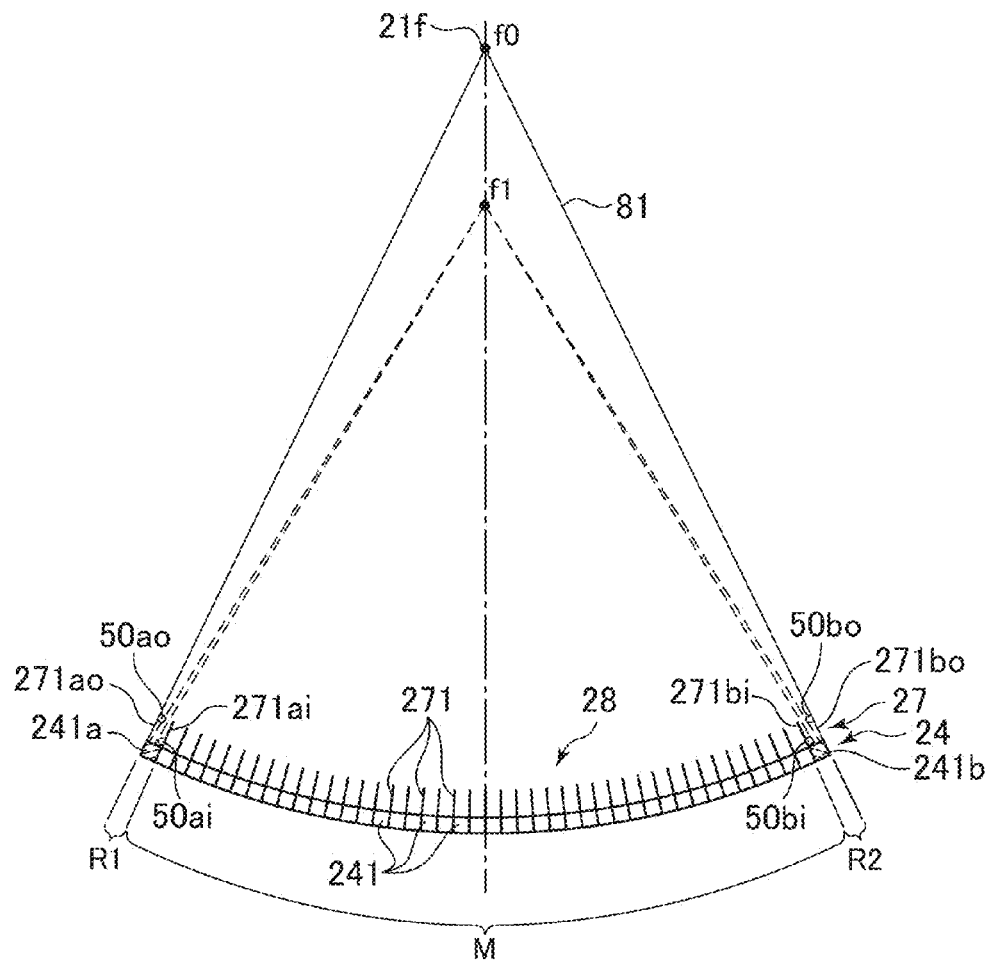
FIGS. 3A and 3B are diagrams depicting an exemplary configuration of an X-ray detection section.
Figure 3B:
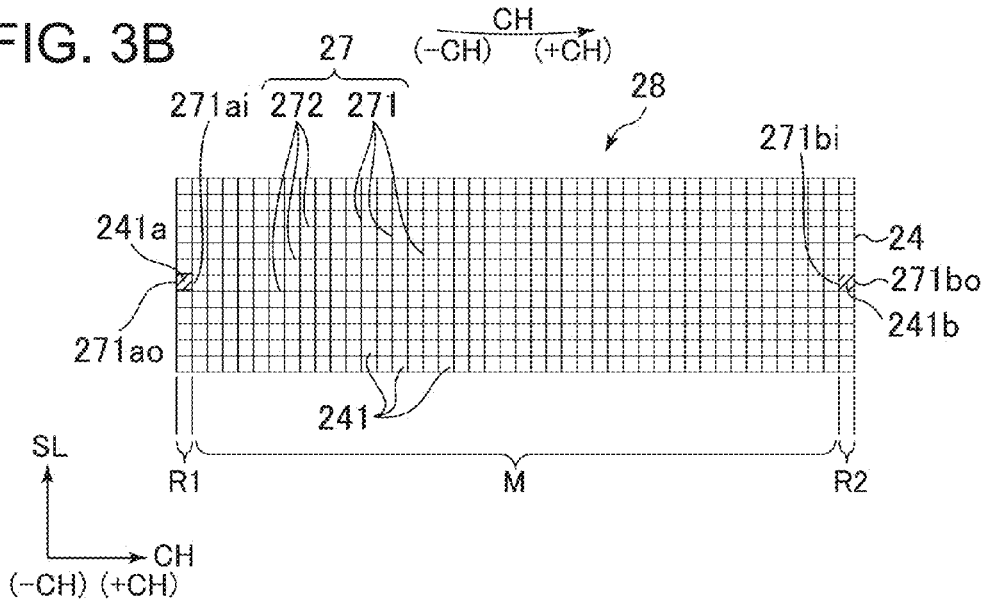

FIG. 2 shows a conceptual diagram of a main part related to an imaging process at the X-ray CT apparatus 100. A configuration example of the X-ray detection section 28 is shown in FIGS. 3A and 3B. FIG. 3A is a diagram (side diagram) as viewed in the z direction, and FIG. B is a diagram (front diagram) as viewed from the X-ray tube 21 side.

As shown in FIG. 2, the main part related to an X-ray projection data correcting process at the X-ray CT apparatus 100 is equipped with the X-ray detection section 28, an X-ray projection data acquisition unit 51, an X-ray projection data correction unit 52, a correction information acquisition unit 53, and an image reconstruction unit 54. The X-ray detection section 28 has an X-ray detector 24 and a collimator 27 which removes scattered X-rays.

The X-ray detector 24 has a configuration in which X-ray detecting elements 241 are arranged in matrix form in the channel and slice directions. The respective X-ray detecting elements 241 are placed along a slope curved surface in such a manner that their detection surfaces face a reference position f0 of an X-ray focal point 21f at the X-ray tube 21. Here, the reference position f0 corresponds to a design ideal position of the X-ray local point. In the X-ray detector 24, the X-ray detecting elements 241 are arranged in, for example, 1000 (channel direction)×150 (slice direction). The detection surface of each X-ray detecting element 241 is approximately square having a width of about 1.025 mm. Incidentally, in FIG. 2, for convenience, the number of the X-ray detecting elements 241 shown is less.

The collimator 27 is provided on the detection surface side of the X-ray detector 24. The collimator 27 is comprised of a plurality of channel direction collimator plates 271, and a plurality of slice direction collimator plates 272. The channel direction collimator plates 271 are provided at the boundaries in the channel direction between the X-ray detecting elements 241 and both ends extending along the channel direction, of the X-ray detector 24 in such a manner that the X-ray detecting elements 241 are divided or separated one by one in the channel direction. The slice direction collimator plates 272 are provided at the boundaries in the slice direction between the X-ray detecting elements 241 and both ends extending along the slice direction, of the X-ray detector 24 in such a manner that the X-ray detecting elements 241 are separated one by one along the slice direction. The channel direction collimator plates 271 and the slice direction collimator plates 272 are provided upright in such a manner that their plate surfaces extend along a radial direction from the reference position f0. The channel direction collimator plates 271 and the slice direction collimator plates 272 are respectively made of a material that absorbs X-rays, such as tungsten, molybdenum, lead or the like.

As shown in FIGS. 3A and 3B, the X-ray detector 24 includes a main region M, and first and second reference regions R1 and R2. The first and second reference regions R1 and R2 are regions that are provided at both ends in the channel direction, of the X-ray detector 24 and irradiated with X-rays which do not penetrate the subject 40. Here, a reference region on the –CH direction side is defined as the first reference region R1, and a reference region on the +CH direction side is defined as the second reference region R2.

The main region M is a region other than these reference regions. Detected data obtained by the X-ray detecting elements 241 lying in the main region M are used for image reconstruction. Data detected by the X-ray detecting elements 241 in the first and second reference regions R1 and R2 are used for correction of the detected data of the main region M. This correction includes a correction for canceling the effects of variations in X-ray intensity, a correction for canceling the effects of variations in the position of the X-ray focal point 21f, etc.

A predetermined first X-ray detecting element 241a in the first reference region R1, and a predetermined second X-ray detecting element 241b in the second reference region R2 are X-ray detecting elements for detecting a positional displacement in the channel direction, of the X-ray focal point 21f as viewed from the reference position f0. In the present example, the first and second X-ray detecting elements 241a and 241b are respectively a single X-ray detecting element and are located at both ends identical in the slice-direction position and aligned along the channel direction.

Figures 5A, 5B:
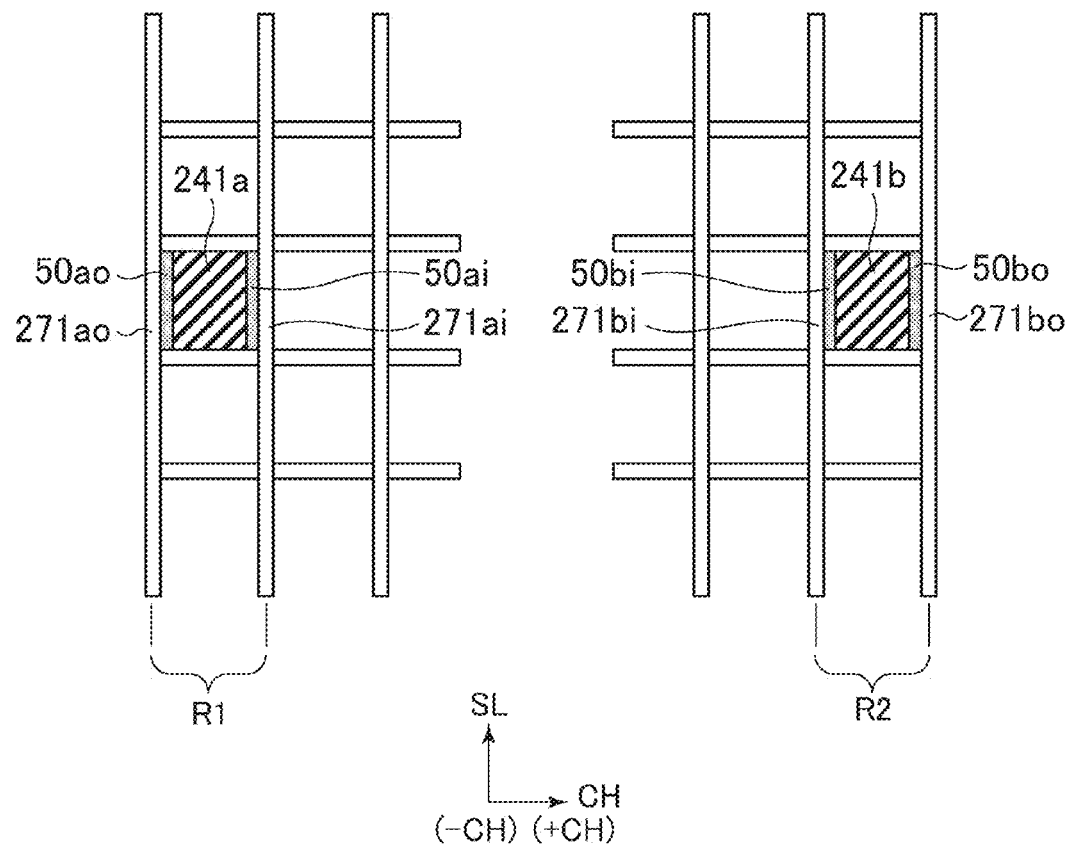
FIGS. 5A and 5B are front enlarged diagrams of the peripheries of the first and second X-ray detecting elements.

Enlarged diagrams of the peripheries of the first and second X-ray detecting elements 241a and 241b are shown in FIGS. 4A, 4B, 5A, and 5B. FIGS. 4A and 4B are each a diagram (side diagram) as viewed in the z direction, and FIGS. 5A and 5B are each a diagram (front diagram) as viewed from the X-ray tube 21 side. Incidentally, the direction that extends to the X-ray focal point is assumed to be an I direction herein.

Now, a channel direction collimator plate placed at an end position on the –CH direction side, of the first X-ray detecting element 241a is called a first outer channel direction collimator plate 271ao. A channel direction collimator plate placed at an end position on the +CH direction side, of the first X-ray detecting element 241a is called a first inner channel direction collimator plate 271ai.

As shown in FIGS. 4A, 4B, 5A, and 5B, a first outer X-ray adsorption member 50ao is provided at the surface on the +CH direction side, of the first outer collimator plate 271ao. Further, a first inner X-ray absorption member 50ai is provided at the surface on the –CH direction side, of the first inner collimator plate 271ai.

The first outer and inner X-ray absorption members 50ao and 50ai are columnar members with their axial directions as the z direction, for example. In the present example, the first outer and inner X-ray absorption members 50ao and 50ai are formed to be approximately circular in their columnar-axis sections, i.e., wire-shaped. The lengths in the z direction, of the first outer and inner X-ray absorption members 50ao and 50ai are approximately identical to the widths in the slice direction, of the first and second X-ray detecting elements 241a and 241b.

The first outer X-ray absorption member 50ao is provided near the X-ray tube 21 with respect to the surface of the first outer collimator plate 271a. The first inner X-ray absorption member 50ai is provided near the first X-ray detecting element 241a with respect to the surface of the first inner collimator plate 271ai.

The first outer X-ray absorption member 50ao is disposed in such a manner that the direction Lao tangential to the first outer X-ray absorption member 50ao and the end near the first X-ray detecting element 241a, of the first outer collimator plate 271ao extends along the radial direction from a virtual position f1 close to the X-ray detector 24 as viewed from the reference position f0. The first inner X-ray absorption member 50ai is disposed in such a manner that the direction Lai tangential to the first inner X-ray absorption member 50ai and the end near the X-ray tube 21, of the first inner collimator plate 271ai extends along the radial direction from the virtual position f1.

With such a configuration, the first outer and inner X-ray absorption members 50ao and 50ai shield against some of X-rays 81 incident to the first X-ray detecting element 241a to limit paths capable of X-ray incidence thereto. As a result, these X-ray absorption members function so as to reach, in defining the paths, substantially approximately the same as where the surfaces of the first outer collimator plate 271ao and the first inner collimator plate 271ai are formed along the radial direction from the virtual position f1 close to the X-ray detector 24 as viewed from the reference position f0.

Likewise, a wire-like second outer X-ray absorption member 50bo with the z direction as its axial direction is provided near the X-ray tube 21 at the surface of a second outer collimator plate 271bo. A wire-like second inner X-ray absorption member 50bi with the z direction as its axial direction is provided near the second X-ray detecting element 241b at the surface of a second inner collimator plate 271bi. The second outer X-ray absorption member 50bo is disposed in such a manner that the direction Lbo tangential to the second outer X-ray absorption member 50bo and the end near the second X-ray detecting element 241b, of the second outer collimator plate 271bo extends along the radial direction from the virtual position f1. The second inner X-ray absorption member 50bi is disposed in such a manner that the direction Lbi tangential to the second inner X-ray absorption member 50bi and the end near the X-ray tube 21, of the second inner collimator plate 271bi extends along the radial direction from the virtual position f1.

The first inner X-ray absorption member 50ai, the first outer X-ray absorption member 50ao, the second inner X-ray absorption member 50bi and the second outer X-ray absorption member 50bo are respectively composed of a material that absorbs X-rays, such tungsten, molybdenum, lead or the like in a manner similar to the collimator plates.

Thus, in the exemplary embodiment, the directions of the virtual surfaces of the channel direction collimator plates for dividing the first and second X-ray detecting elements 241a and 241b in the channel direction extend along the radial direction from the virtual position f1. Therefore, shadows in X-ray radiation fields generated at the detection surfaces of these X-ray detecting elements change differently according to an actual position fx of the X-ray focal point 21f at the first X-ray detecting element 241a on one end side as viewed in the channel direction and the second X-ray detecting element 241b on other end side. That is, in the first X-ray detecting element 241a, the size of the radiation field of the X-rays becomes maximum when the X-ray focal point 21f is located on the other end side as viewed in the channel direction, whereas in the second X-ray detecting element 241b, the size of the radiation field of the X-rays becomes maximum when the X-ray focal point 21f is located on one end side as viewed in the channel direction. As a result, the positions in the channel direction of the X-ray focal point 21f can be reflected on the sizes of the radiation fields at the detection surfaces of the first and second X-ray detecting elements 241a and 241b. The position in the channel direction, of the X-ray focal point 21f can be detected in high resolution from the outputs of the first and second X-ray detecting elements 241a and 241b.

A description will now be made of a method for detecting the position of the X-ray focal point and correcting X-ray projection data.

FIGS. 6 through 13 are diagrams for describing the principle of detecting the position of the X-ray focal point.

Now consider where X-rays are applied onto the detection surfaces of the first and second X-ray detecting elements 241a and 241b while changing the position in the channel direction, of the X-ray focal point 21f.

Figure 6:
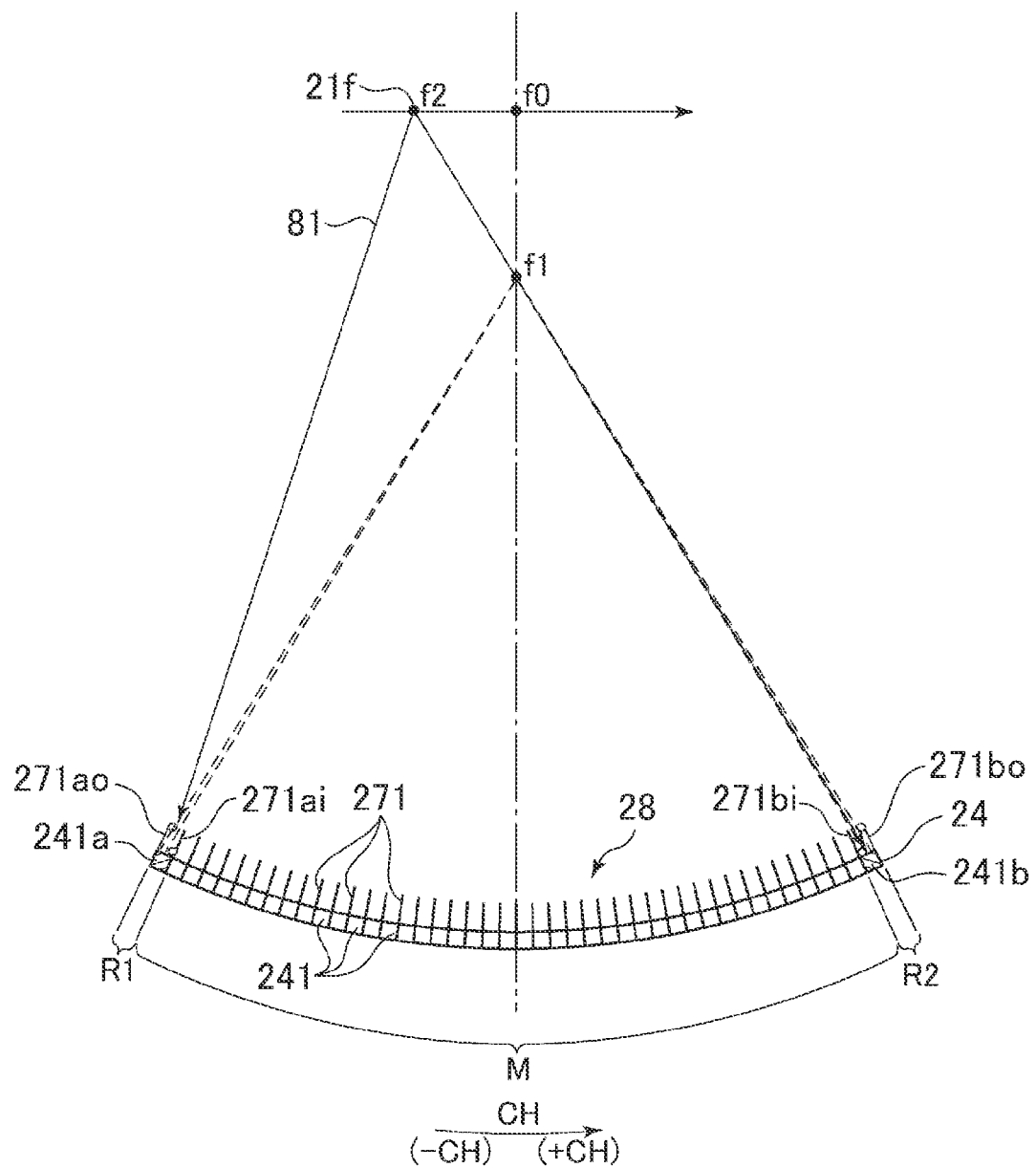
FIG. 6 is a diagram showing the relationship between X-rays and the X-ray detection section where an X-ray focal point is located on the –CH direction side as viewed from a reference position.

First assume where as shown in FIG. 6, the X-ray focal point 21f is placed in a position f2 located on the −CH direction side as viewed from the reference position f0. Here, the position f2 is a position on a straight line that substantially connects a virtual position f1 and the second X-ray detecting element 241b.

Figure 7A:
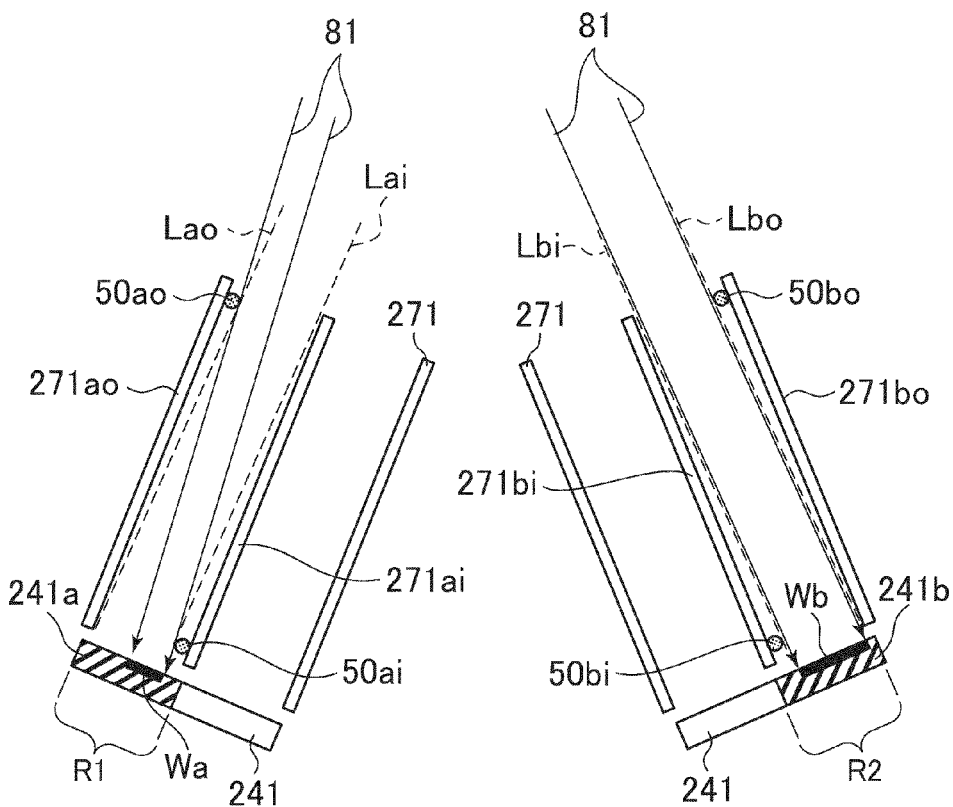
FIGS. 7A and 7B are side enlarged diagrams of the peripheries of the first and second X-ray detecting elements where the X-ray focal point is located on the –CH direction side as viewed from the reference position.
Figure 7B:
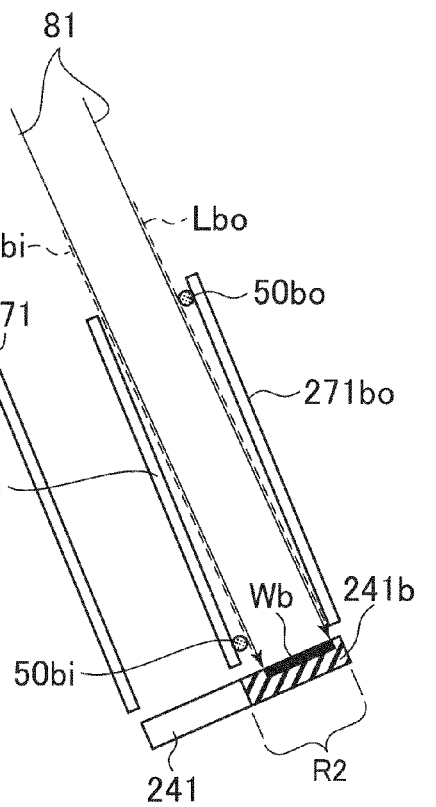

In this case, as shown in FIGS. 7A and 7B, the detection surface of the second X-ray detecting element 241b can undergo or receive X-rays 81 almost without the X-rays 81 being shielded by the second outer X-ray absorption member 50bo and the second inner X-ray absorption member 50bi. That is, an X-ray radiation field Wb at the detection surface of the second X-ray detecting element 241b becomes maximum. In the detection surface of the first X-ray detecting element 241a, however, the X-rays 81 are blocked off by not only the first outer collimator plate 271ao and the first inner collimator plate 271ai but also the first outer X-ray absorption member 50ao and the first inner X-ray absorption member 50ai. Therefore, an X-ray radiation field Wa at the detection surface of the first X-ray detecting element 241a becomes very small.

Figure 8:
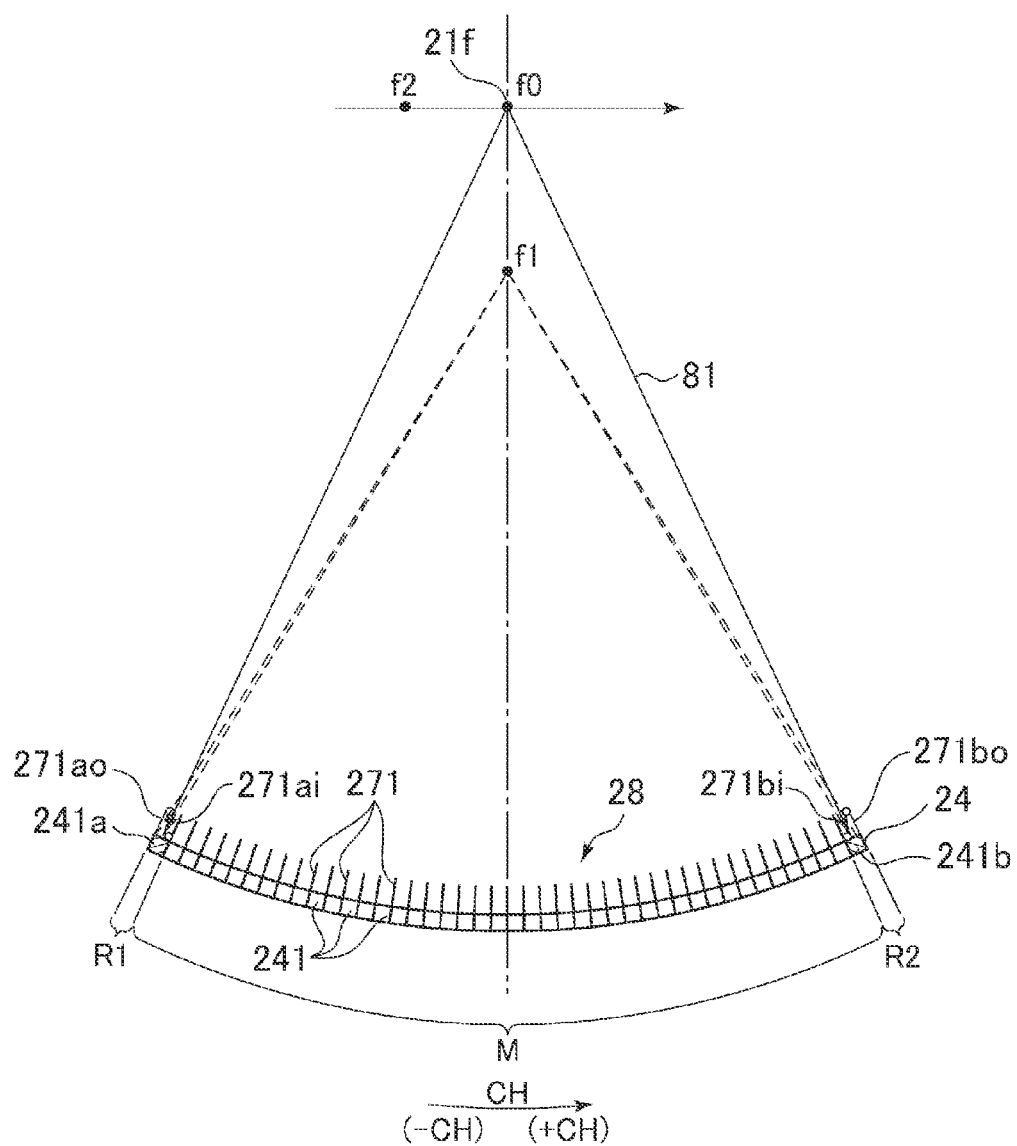
FIG. 8 is a diagram showing the relationship between X-rays and the X-ray detection section where the X-ray focal point is placed in the reference position.

Next, assume where as shown in FIG. 8, the X-ray focal point 21f gradually moves from the position f2 to the reference position f0.

Figures 9A, 9B:
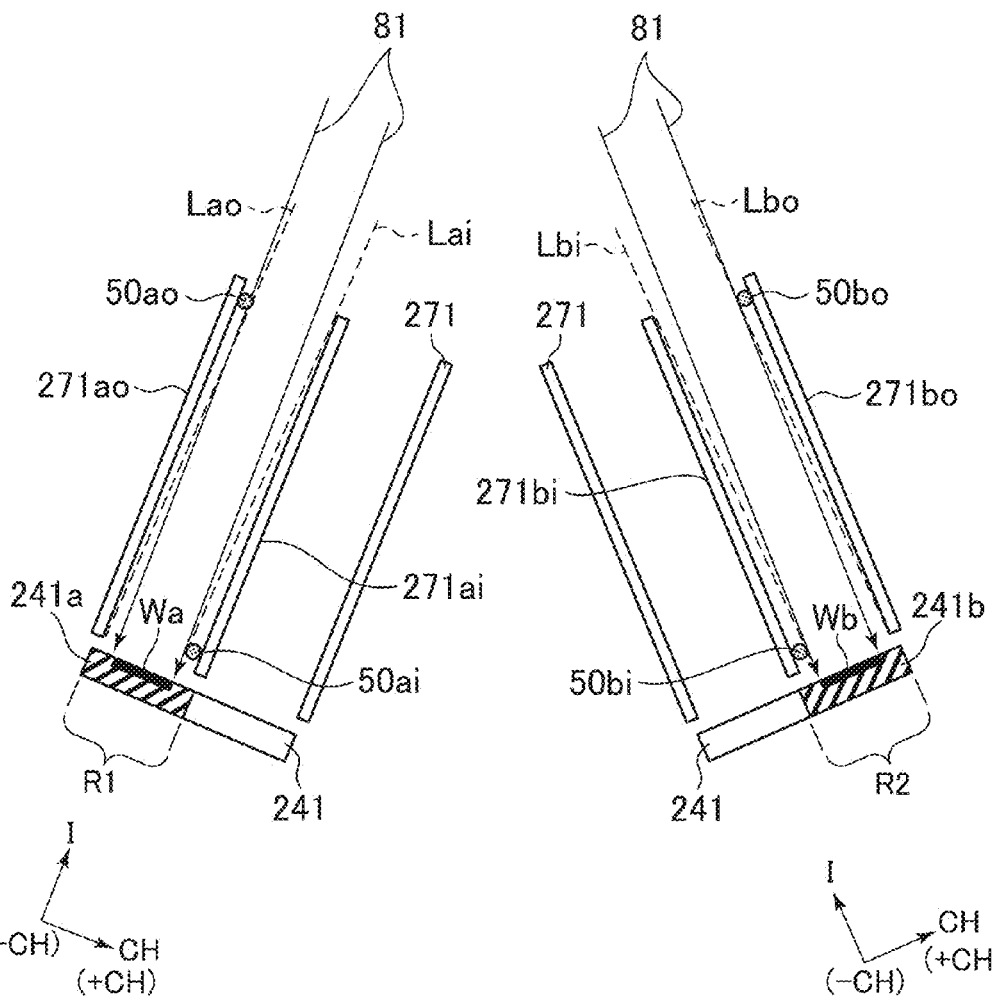
FIGS. 9A and B are side enlarged diagrams of the peripheries of the first and second X-ray detecting elements where the X-ray focal point is placed in the reference position.

In this case, the range in which the X-rays 81 are blocked by the second outer X-ray absorption member 50bo and the second inner X-ray absorption member 50bi becomes wide at the detection surface of the second X-ray detecting element 241b. That is, the X-ray radiation field Wb at the detection surface of the second X-ray detecting element 241b becomes gradually small. On the other hand, the range in which the X-rays are blocked by the first outer X-ray absorption member 50ao and the first inner X-ray absorption member 50ai becomes narrow at the detection surface of the first X-ray detecting element 241a. That is, the X-ray radiation field Wa at the detection surface of the first X-ray detecting element 241a becomes gradually large. When the X-ray focal point 21f is placed in the reference position f0, the X-ray radiation fields Wa and Wb at the detection surfaces of the first and second X-ray detecting elements 241a and 241b both become a size of the same degree as shown in FIGS. 9A and 9B.

Figure 10:
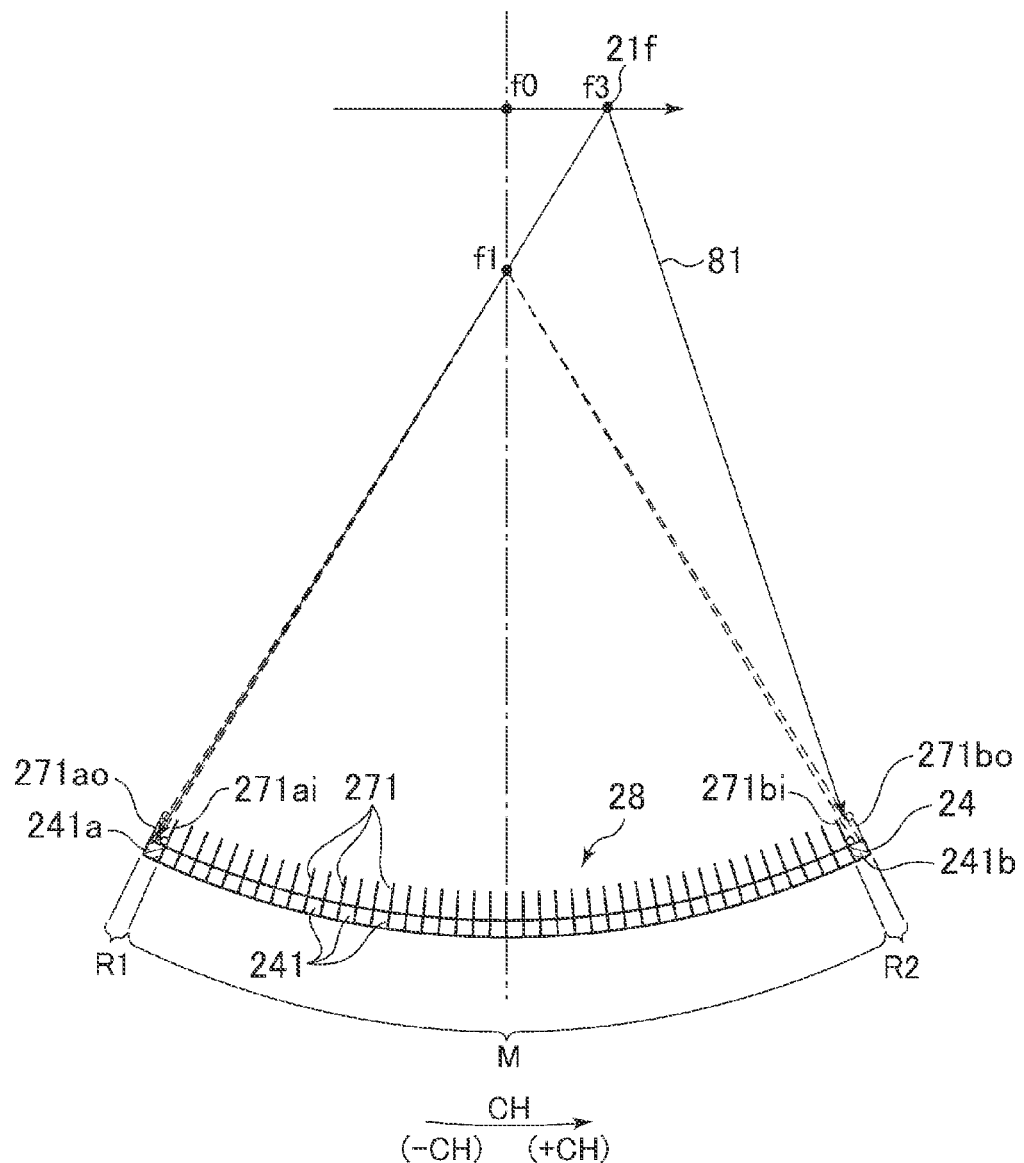
FIG. 10 is a diagram showing the relationship between X-rays and the X-ray detection section where the X-ray focal point is located on the +CH direction side as viewed from the reference position.

Next assume where as shown in FIG. 10, the X-ray focal point 21f is further moved in the +CH direction and placed in a position f3 lying on the +CH direction side as viewed from the reference position f0. Here, the position f3 is a position on a straight line that substantially connects a virtual position f1 and the first X-ray detecting element 241a.

Figures 11A, 11B:
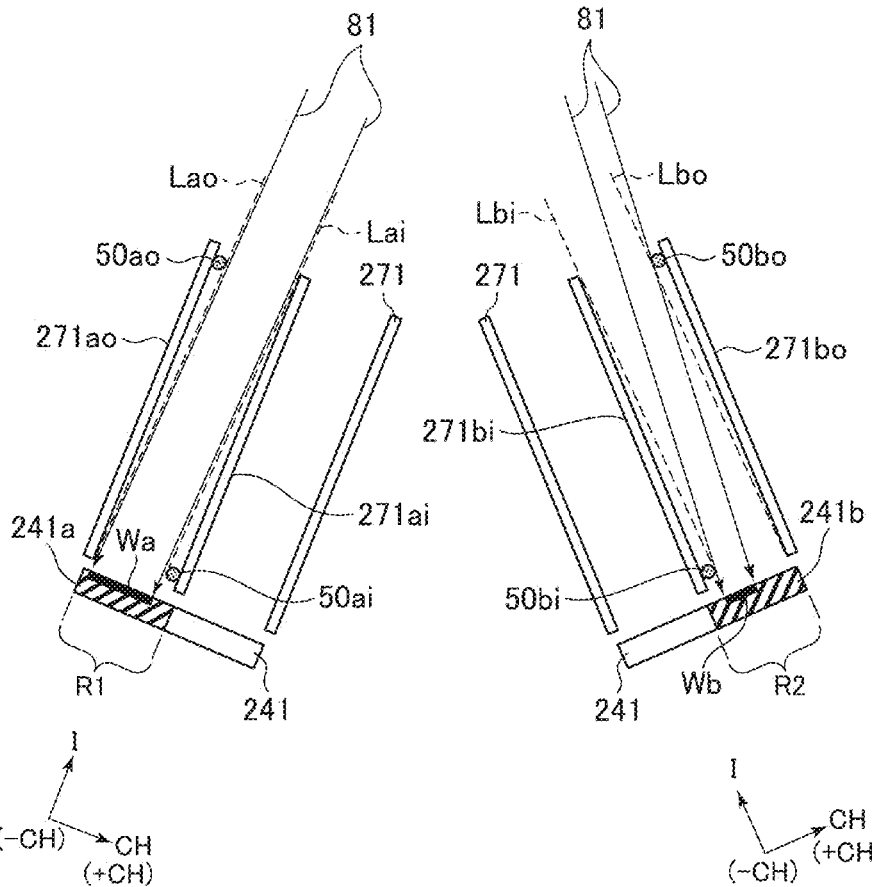
FIGS. 11A and 11B are side enlarged diagrams of the peripheries of the first and second X-ray detecting elements where the X-ray focal point is located on the +CH direction side as viewed from the reference position.

When the X-ray focal point 21f is moved in the +CH direction from the reference position f0, the X-ray radiation field Wa at the detection surface of the first X-ray detecting element 241a becomes further small, and the X-ray radiation field Wb at the detection surface of the second X-ray detecting element 241b becomes further large. When the X-ray focal point 21f is placed in the position f3 as shown in FIGS. 11A and 11B, the detection surface of the first X-ray detecting element 241a can undergo X-rays 81 almost without the X-rays 81 being blocked by the first outer X-ray absorption member 50ao and the first inner X-ray absorption member 50ai. That is, the X-ray radiation field Wa at the detection surface of the first X-ray detecting element 241a becomes maximum. On the other hand, at the detection surface of the second X-ray detecting element 241b, the X-rays 81 are blocked by not only the second outer collimator plate 271bo and the first inner collimator plate 271bi but also the second outer X-ray absorption member 50bo and the second inner X-ray absorption member 50bi. Therefore, the X-ray radiation field Wb at the detection surface of the second X-ray detecting element 241b becomes very small.

Figure 12:
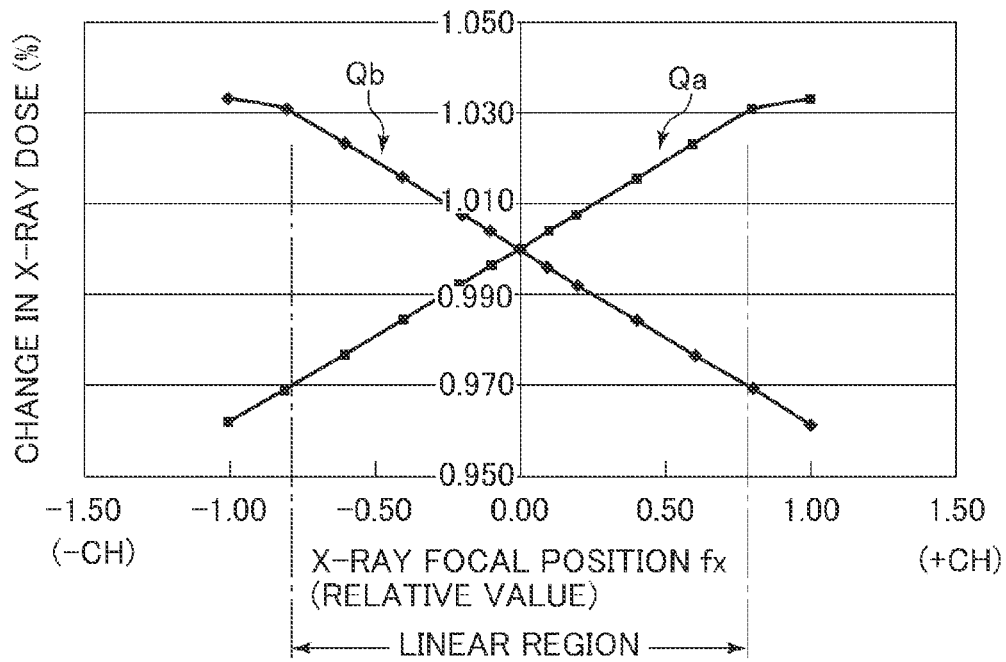
FIG. 12 is a graph showing the relationship between the position of the X-ray focal point and X-ray doses received at the first and second X-ray detecting elements.
Figure 13:
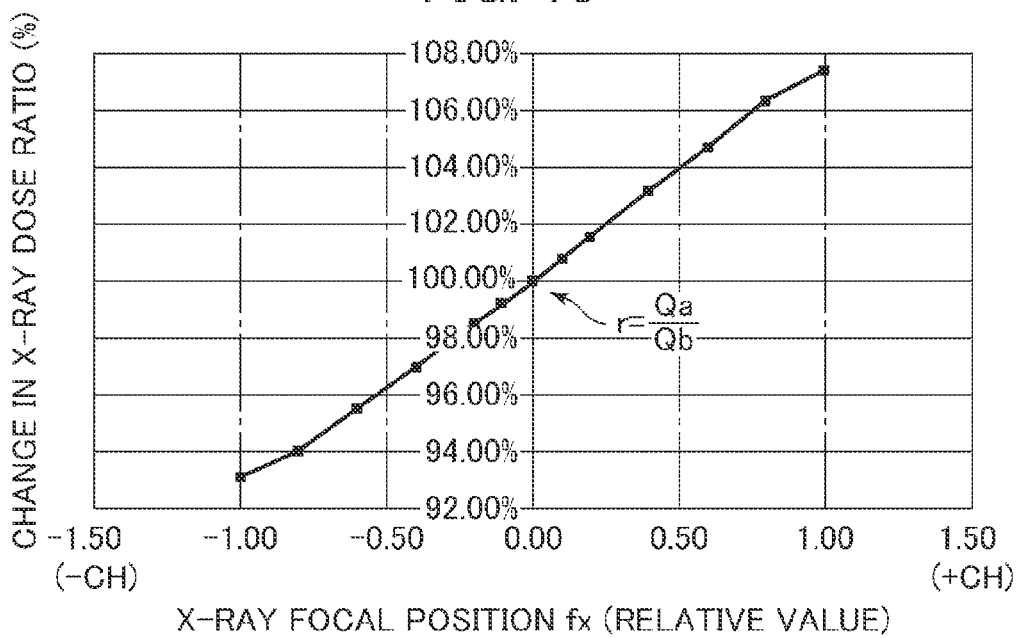
FIG. 13 is a graph showing the relationship between the position of the X-ray focal point and the ratio between X-ray doses received at the first and second X-ray detecting elements.

Plotting X-ray doses Qa and Qb received at the detection surfaces of the first and second X-ray detecting elements 241a and 241*b* every position fx of the X-ray focal point 21*f* yields such graphs as shown in FIG. 12. As is understood from the graphs, variations in the position of the X-ray focal point 21*f* are reflected on the X-ray doses Qa and Qb received at the detection surfaces of the first and second X-ray detecting elements 241*a* and 241*b*. Thus, the balance of the X-ray doses Qa and Qb received at the detection surfaces of the first and second X-ray detecting elements 241*a* and 241*b*, e.g., the ratio r of the X-ray dose Qa received by the first X-ray detecting element 241*a* to the X-ray dose Qb received by the second X-ray detecting element 241*b* becomes a nearly linearly increasing function as shown in FIG. 13. The X-ray dose ratio r and the X-ray focal position fx correspond to each other on a one-to-one basis.

The relation shown in FIG. 13 is acquired in advance as a function table T1 of the entire X-ray detector 24, and at the same time output responses to the X-ray focal position fx are determined as an inherent table T2*i* with respect to the individual X-ray detecting elements 241 of the X-ray detector 24. Even though the position of the X-ray focal point 21*f* varies upon imaging if done in this way, the position thereof, i.e., the X-ray focal position fx can be determined using the outputs of the first and second X-ray detecting elements 241*a* and 241*b* and the function table T1. Applying the determined X-ray focal position fx to the table T2*i* makes it possible to provide correction coefficients for all the X-ray detecting elements 241 individually and in real time.

This calculation is not affected by sensitivity of each X-ray detecting element 241 relative to the variations in the position of the X-ray focal point 21*f*. Therefore, even if the X-ray detector 24 is installed in a position placed face to face to the X-ray tube 21, which is most susceptible to the variations in the position of the X-ray focal point 21*f*, a stable output can be obtained.

In the exemplary embodiment, the correction information acquisition unit 53 controls the respecting parts to thereby acquire detected data at the first and second X-ray detecting elements 241*a* and 241*b* and the respective X-ray detecting elements 241*i* in the main region M while changing the position in the channel direction of the X-ray focal point 21*f*. The function table T1 (discussed above) is determined from changes in the detected data at the first and second X-ray detecting elements 241*a* and 241*b* at the time that the position fx in the channel direction of the X-ray focal point 21*f* is changed, and stored in the correction information acquisition unit 53. A correction coefficient ki for canceling the effects of the detected data due to the variations in the X-ray focal position fx is determined as a function ki (fx) of the X-ray focal position fx from the changes in the detected data for every X-ray detecting element 241*i* in the main region M at the time that the position fx in the channel direction of the X-ray focal point 21*f* is changed. The so-determined ki is stored in the correction information acquisition unit 53. Incidentally, control on the movement of the X-ray focal point 21*f* can be achieved by electromagnetically changing the orbit of an electron beam to a target at the X-ray tube 21, for example.

The X-ray projection data acquisition unit 51 controls the respective parts to thereby scan the subject 40 so as to acquire X-ray projection data Pv of respective views.

The X-ray projection data correction unit 52 determines an X-ray dose ratio rv from the outputs of the first and second X-ray detecting elements 241*a* and 241*b* for every acquired X-ray projection data Pv of views v and applies the same to the function table T1 to thereby determine a position fxv of the X-ray focal point 21*f* corresponding to each view v. Data pvi detected by each X-ray detecting element 241*i*, which makes up the X-ray projection data Pv of each view v intended for processing is corrected using the correction coefficient ki (fxv).

The image reconstruction unit 54 performs image reconstruction by backprojection processing or the like using the corrected X-ray projection data.

Thus, the flow of processing at the X-ray CT apparatus according to the exemplary embodiment will be explained.

Figure 14:
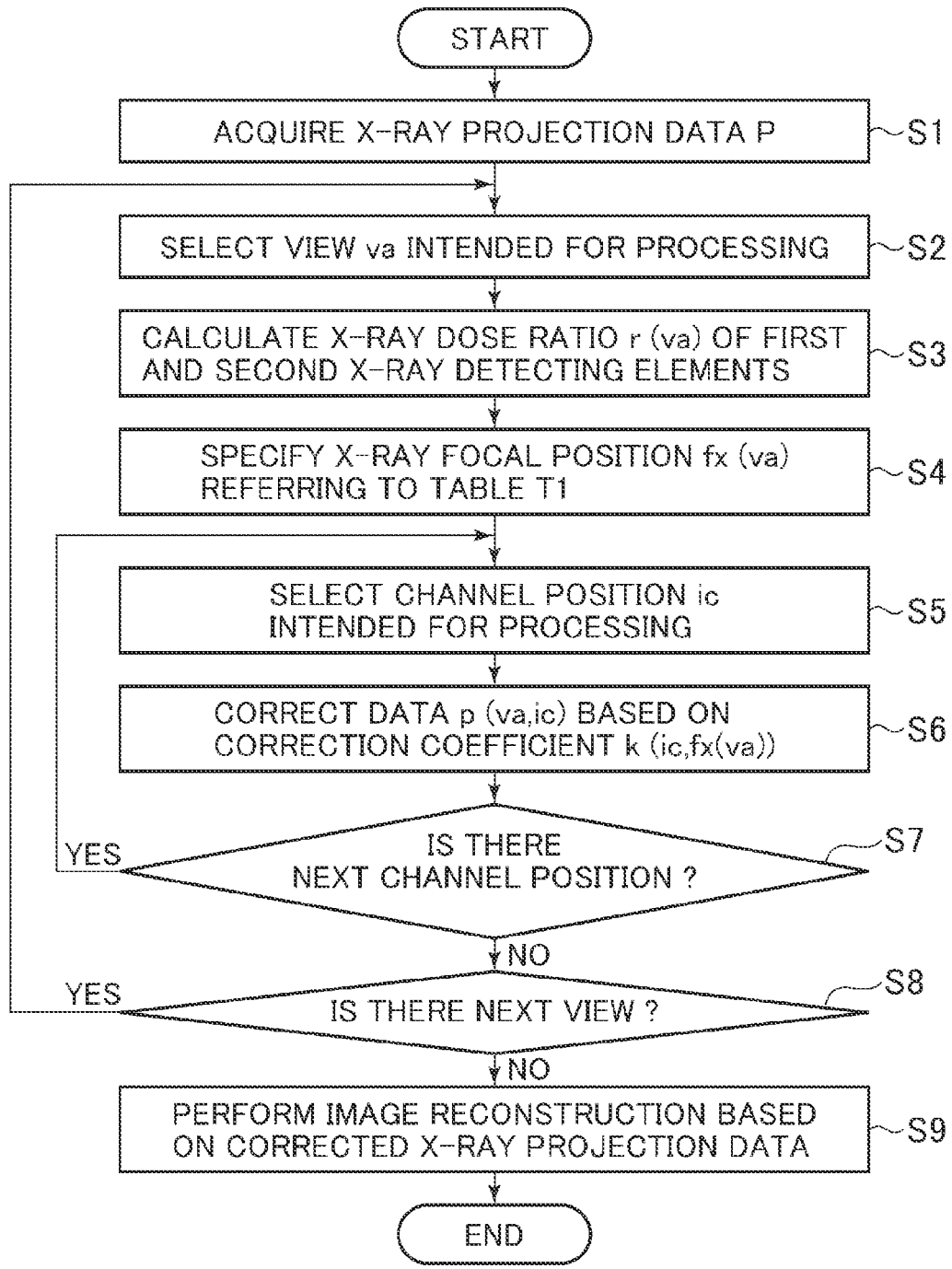
FIG. 14 is flow diagram illustrating the flow of an exemplary imaging process at the X-ray CT apparatus.

FIG. 14 is a flow diagram showing the flow of exemplary imaging processing at the X-ray CT apparatus.

At Step S1, the X-ray projection data acquisition unit 51 scans the subject to acquire X-ray projection data Pv of plural views v.

At Step S2, the X-ray projection data correction unit 52 selects a view va of X-ray projection data, which is intended for processing.

At Step S3, the X-ray projection data correction unit 52 determines an X-ray dose ratio rva from the ratio of detected signal values of both first and second X-ray detecting elements 241*a* and 241*b* at the selected X-ray projection data Pva of view va in consideration of sensitivities of their X-ray detecting elements.

At Step S4, the X-ray projection data correction unit 52 applies the X-ray dose ratio rva to the function table T1 previously determined by the correction information acquisition unit 53 to thereby determine an X-ray focal point position fx (va) corresponding to the view va.

At Step S5, the X-ray projection data correction unit 52 selects a channel position ic for detected data intended for processing.

At Step S6, the X-ray projection data correction unit 52 corrects the selected view va and the detected data p (va, ic) of the channel position ic using the correction coefficient k (ic, fx (va)) previously determined by the correction information acquisition unit 53.

At Step S7, the X-ray projection data correction unit 52 determines whether there is a channel position to be next selected. If the answer is found to be Yes, the imaging process returns to Step S4, where a new channel position is selected. If the answer is found to be No, the imaging process proceeds to the next Step S8.

At Step S8, the X-ray projection data correction unit 52 determines whether there is a view to be next selected. If the answer is found to be Yes, the imaging process returns to Step S2, where a new view is selected. If the answer is found to be No, the imaging process proceeds to Step S9.

At Step S9, the image reconstruction unit 54 performs image reconstruction based on the corrected X-ray projection data of plural views.

Thus, according to the exemplary embodiment, the first and second X-ray detecting elements 241*a* and 241*b* are separated in the channel direction by the channel direction collimator plates provided with the X-ray absorption members at their surfaces as described above. Therefore, at the first X-ray detecting element 241*a*, the size of the X-ray radiation field becomes maximum when the X-ray focal point 21*f* is located on the other end side in the channel direction, whereas at the second X-ray detecting element 241*b*, the size of the X-ray radiation field becomes maximum when the X-ray focal point 21*f* is located on one end side in the channel direction. As a result, the position of the X-ray focal point 21*f* can be determined in high resolution based on the outputs of the first and second X-ray detecting elements 241*a* and 241*b*, thus making it possible to correct the effects of small variations in the position of the X-ray focal point 21*f* to the X-ray projection data. This correction enables suppression of degradation in image quality of a reconstructed image.

According to the exemplary embodiment, since the surfaces of the collimator plates in the main region M respectively remain in the state extending along the radial direction from the reference position f0 of the X-ray focal point 21f, X-ray utilization efficiency of each X-ray detecting element in the main region M is not reduced.

According to the exemplary embodiment as well, parts to be added on a hard basis are simple as compared to the conventional case, and an increase in part cost is relatively low.

Further, according to the exemplary embodiment, the addition of such a correction algorithm as described above enables suppression of the effects of variations in the accuracy of installation of the collimator plates. It is therefore possible to relax the specs related to the accuracy of installation of the collimator plates. A reduction in so-called scrap cost can also be expected.

Incidentally, the present invention is not limited to the exemplary embodiment, but can be modified in various forms within the scope not departing from the gist of the invention.

Figure 15:
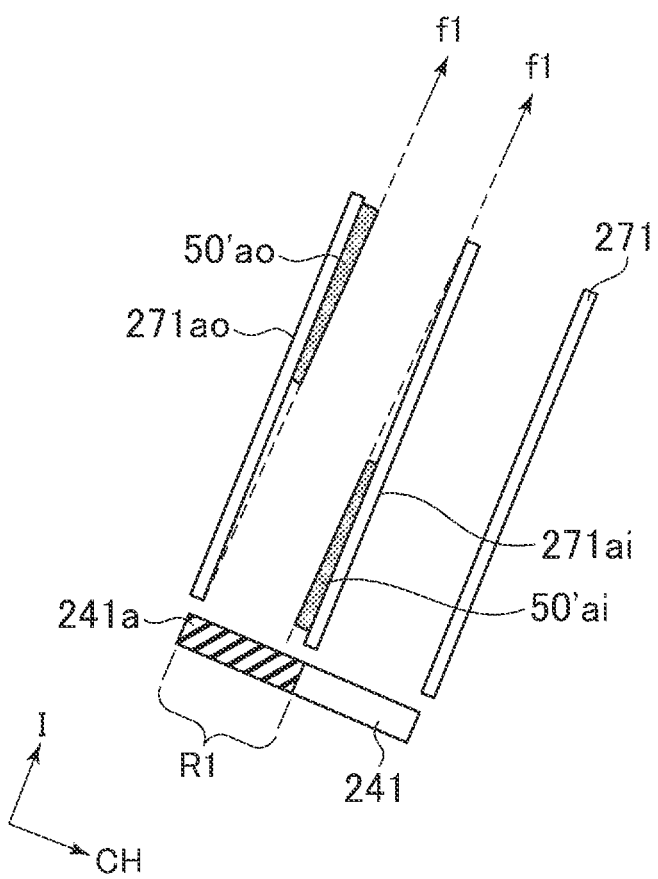
FIG. 15 is a diagram showing an example in which X-ray absorption members trapezoidal in axial section are respectively provided on the surfaces of collimator plates.

For example, each of the X-ray absorption members provided onto the collimator plates is not limited to such a wire-like member as described above, but may be configured as a columnar member with its axial direction as the z direction. In this case, the X-ray absorption members can be formed in such a manner that their columnar-axis sections become elliptical or polygonal (e.g., triangular, trapezoidal or the like) that change in thickness along the radial direction from the virtual position f1. X-ray absorption members 28'ao and 28'ai whose axial sections are trapezoidal are shown in FIG. 15 by way of example.

For example, the first and second X-ray detecting elements separated by the collimator plates provided with the X-ray absorption members may respectively be positioned on one and other end sides of the X-ray detector 24 in the channel direction, or may be placed in positions other than both ends.

Figures 16A, 16B:
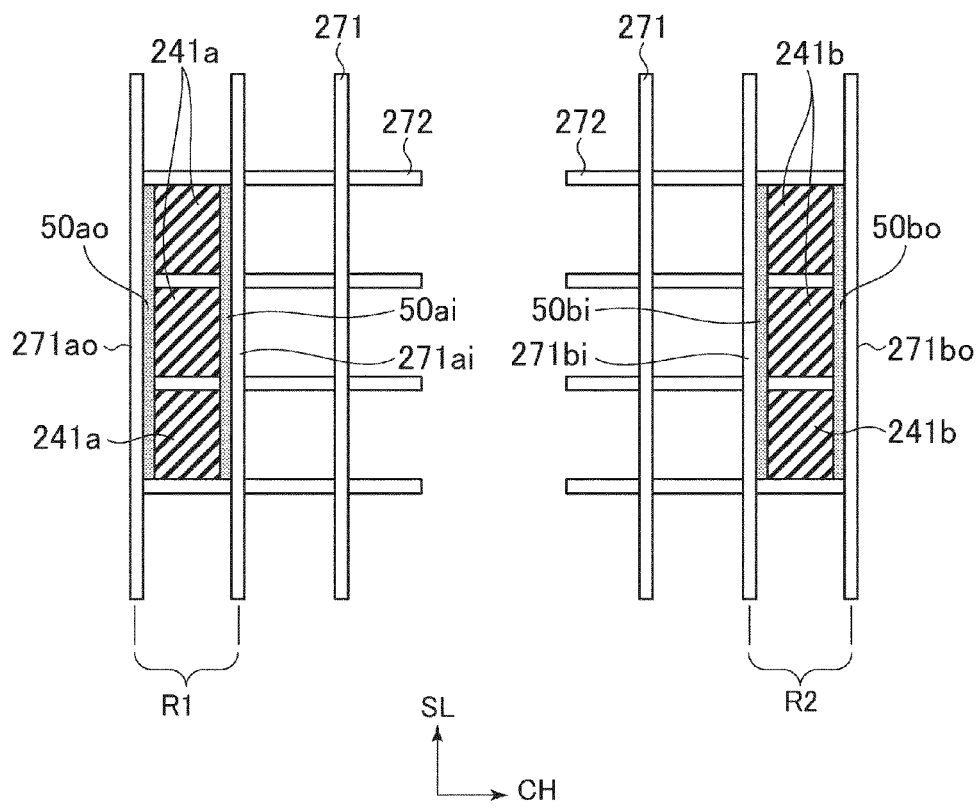
FIGS. 16A and 16B are diagrams illustrating an example in which first and second X-ray detecting elements are respectively configured as a plurality of X-ray detecting elements arranged in a slice direction.
Figure 17A:
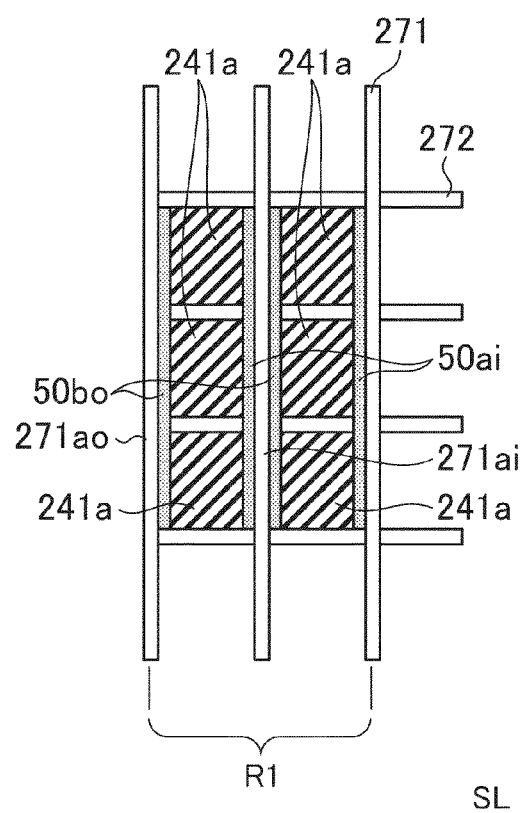
FIGS. 17A and 17B are diagrams an example in which first and second X-ray detecting elements are respectively configured as a plurality of X-ray detecting elements arranged in channel and slice directions.
Figure 17B:
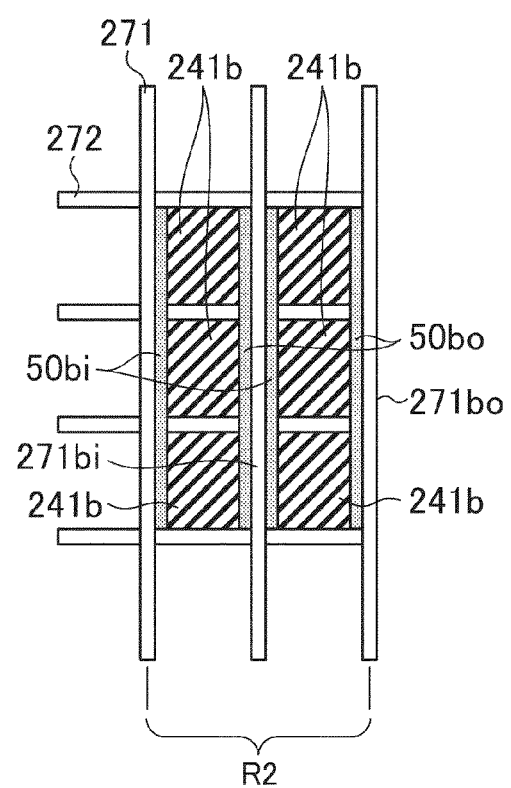

For example, such first and second X-ray detecting elements may each include a plurality of X-ray detecting elements. As shown in FIGS. 16A and 16B, for example, the first and second X-ray detecting elements 241a and 241b may respectively be configured as a plurality of X-ray detecting elements arranged in the slice direction. As shown in FIGS. 17A and 17B, for example, the first and second X-ray detecting elements 241a and 241b may respectively be configured as a plurality of X-ray detecting elements arranged in the channel and slice directions.

In this case, the average value of detected signal values of the plural X-ray detecting elements corresponding to the first X-ray detecting elements, and the average value of detected signal values of the plural X-ray detecting elements corresponding to the second X-ray detecting elements are determined. Next, an X-ray dose ratio r is determined from the ratio between the average value of detected signal values of the first X-ray detecting elements, and the average value of detected signal values of the second X-ray detecting elements. Then, the position of the X-ray focal point 21f in the channel direction is determined with reference to the function table T1 indicative of the relation of correspondence between the X-ray dose ratio r and the X-ray focal position fx. If done in this way, it is possible to reduce noise components contained in the detected data of the X-ray detecting elements and reduce the effects of variations in the accuracy of installation of the collimator plates.

In the exemplary embodiment, for example, the function table T1 indicative of the relation of correspondence between the X-ray dose ratio r and the X-ray focal position fx related to the first and second X-ray detecting elements at the specific structure portion is determined. The X-ray dose ratio r is determined from the actually-measured detected signal value ratio, and the X-ray focal position fx is determined with reference to the function table T1. As another method, however, there may be used, for example, a method of directly or indirectly determining an X-ray focal position fx from some characteristic amount indicative of the balance of detected signal values of first and second X-ray detecting elements.

In the exemplary embodiment as well, for example, the channel direction collimator plates 271 are arranged in the channel direction. The movement in the channel direction, of the X-ray focal point 21f is detected based on the detected signal values of the first and second X-ray detecting elements 241a and 241b at both ends in the channel direction, and thereby the fluctuations in X-ray projection data due to the focal movement in the channel direction are corrected. A configuration similar to this is however applied in the slice direction to detect movement of the X-ray focal point 21f in the slice direction, whereby fluctuations in X-ray projection data due to the focal movement in the slice direction can also be corrected. Alternatively, the above configuration can also be applied simultaneously to both of the channel and slice directions.

Further, in the exemplary embodiment, for example, the detected data of the first and second X-ray detecting elements 241a and 241b are obtained from the X-ray projection data acquired by the actual scan of the subject, and the movement of the X-ray focal point is detected using the X-ray projection data. When a scan different from the actual scan, e.g., a scan for air calibration prior to the actual scan is however performed, detected data of the first and second X-ray detecting elements 241a and 241b are acquired and the movement of the X-ray focal point 21f may be detected using the data. Since the X-ray focal point 21f often moves slowly in time in general, it is sufficiently possible to correct the X-ray projection data even if the timing provided to acquire the detected data used for correction, of the first and second X-ray detecting elements 241a and 241b, and the timing provided to acquire the X-ray projection data used for image reconstruction are slightly shifted relative to each other. The scan for air calibration can also bring about an advantage in that since the subject 40 is not placed in the imaging space, the effects of scattered radiation to the detected data can be prevented.

Although the exemplary embodiment is of an X-ray CT apparatus, the embodiments described herein can be applied to a PET-CT apparatus or SPECT-CT apparatus in which the X-ray CT apparatus and PET or SPECT are combined together, etc.

The invention claimed is:

1. A radiation imaging apparatus comprising:
   a radiation source configured to emit radiation to a target for imaging from a first focal point corresponding to a radiation focal point;
   a plurality of radiation detecting elements disposed opposite to the radiation source and arranged in a channel direction;
   a plurality of collimator plates provided along the channel direction on detection surface sides of the radiation detecting elements so as to separate the radiation detecting elements in the channel direction, the collimator plates including radiation absorption members at surfaces of at least one first collimator plate located on a first end side of the collimator plates and at least one second collimator plate located on a second end side of the collimator plates such that radiation shielding effects of the first and second collimator plates become substantially equivalent when the surfaces of the first and second collimator plates are located along a radial direction from a second focal point different from the first focal point; and a data acquisition unit configured to acquire radiation projection data for image reconstruction from the radiation detecting elements.

2. A radiation imaging apparatus according to claim 1, wherein the radiation absorption members are located on opposing plate surfaces of a pair of first collimator plates that border a first radiation detecting element on the first end side, and located on opposing plate surfaces of a pair of second collimator plates that border a second radiation detecting element on the second end side, wherein the radiation absorption members on the pair of first collimator plates are positioned such that a first line tangent to an end proximate the radiation source of a first opposing plate of the pair of first collimator plates and tangent to the radiation absorption member on the first opposing plate, and a second line tangent to an end distant from the radiation source of a second opposing plate of the pair of first collimator plates and tangent to the radiation absorption member on the second opposing plate each extend along the radial direction from the second focal point, wherein the second focal point is closer to the radiation detecting elements than the first focal point, and wherein the radiation absorption members on the pair of second collimator plates are positioned such that a third line tangent to an end proximate the radiation source of a third opposing plate of the pair of second collimator plates and tangent to the radiation absorption member on the third opposing plate, and a fourth line tangent to an end distant from the radiation source of a fourth opposing plate of the pair of second collimator plates and tangent to the radiation absorption member on the fourth opposing plate each extend along the radial direction from the second focal point.

3. A radiation imaging apparatus according to claim 2, further comprising a correcting unit configured to correct effects of a movement of the first focal point on radiation projection data, the radiation projection data corrected based on outputs of the first and second radiation detecting elements.

4. A radiation imaging apparatus according to claim 3, wherein the correcting unit is configured to correct the radiation projection data, based on a balance between the outputs of the first and second radiation detecting elements.

5. A radiation imaging apparatus according to claim 4, wherein the correcting unit is configured to correct the radiation projection data, based on a ratio between the outputs of the first and second radiation detecting elements.

6. A radiation imaging apparatus according to claim 5, wherein the correcting unit is configured to correct the radiation projection data, based on a relation between the ratio of the outputs of the first and second radiation detecting elements and sensitivities of the respective radiation detecting elements, and the output ratio actually measured.

7. A radiation imaging apparatus according to claim 6, further comprising acquisition unit configured to acquire information indicative of the relation by:

moving the first focal point to a plurality of positions different from one another, and detecting, at each position, radiation emitted from the first focal point using the radiation detecting elements.

8. A radiation imaging apparatus according to claim 2, wherein the first radiation element is located at a first end along the channel direction of the radiation detecting elements, and the second radiation detecting element is located at a second end along the channel direction of the radiation detecting elements.

9. A radiation imaging apparatus according to claim 2, wherein the radiation detecting elements are arranged in the channel and slice directions, and wherein the first and second radiation detecting elements each include two or more radiation detecting elements having a different position in the slice direction.

10. A radiation imaging apparatus according to claim 1, wherein each of the radiation absorption members is a columnar member with a slice direction as its axial direction.

11. A radiation imaging apparatus according to claim 10, wherein the radiation absorption members have at least one of a circular and an ellipsoidal columnar-axis section.

12. A radiation imaging apparatus according to claim 10, wherein the radiation absorption members have columnar-axis sections that change in thickness along the radial direction from the second focal point.

13. A radiation detecting apparatus comprising:

a plurality of radiation detecting elements disposed opposite to a radiation source configured to emit radiation to a target for imaging from a first focal point corresponding to a radiation focal point, the plurality of radiation detecting elements arranged in at least a channel direction; and a plurality of collimator plates provided along the channel direction on detection surface sides of the radiation detecting elements so as to separate the radiation detecting elements in the channel direction, the collimator plates including radiation absorption members at surfaces of at least one first collimator plate located on a first end of the collimator plates and at least one second collimator plate located on a second end side of the collimator plates such that radiation shielding effects of the first and second collimator plates become substantially equivalent when the surfaces of the first and second collimator plates are located along a radial direction from a second local point different from the first focal point.

14. A radiation detecting apparatus according to claim 13, wherein the radiation absorption members are located on opposing plate surfaces of a pair of first collimator plates that border a first radiation detecting element on the first end side, and located on opposing plate surfaces of a pair of second collimator plates that border a second radiation detecting element on the second end side, wherein the radiation absorption members on the pair of first collimator plates are positioned such that a first line tangent to an end proximate the radiation source of a first opposing plate of the pair of first collimator plates and tangent to the radiation absorption member on the first opposing plate, and a second line tangent to an end distant from the radiation source of a second opposing plate of the pair of first collimator plates and tangent to the radiation absorption member on the second opposing plate each extend along the radial direction from the second focal point, wherein the second focal point is closer to the radiation detecting elements than the first focal point, and wherein the radiation absorption members on the pair of second collimator plates are positioned such that a third line tangent to an end proximate the radiation source of a third opposing plate of the pair of second collimator plates and tangent to the radiation absorption member on the third opposing plate, and a fourth line tangent to an end distant from the radiation source of a fourth opposing plate of the pair of second collimator plates and tangent to the radiation absorption member on the fourth opposing plate each extend along the radial direction from the second focal point.

15. A radiation detecting apparatus according to claim 14, wherein the first radiation element is located at a first end along the channel direction of the radiation detecting elements, and the second radiation detecting element is located at a second end along the channel direction of the radiation detecting elements.

16. A radiation detecting apparatus according to claim 14, wherein the radiation detecting elements are arranged in the channel and slice directions, and wherein the first and second radiation detecting elements each include two or more radiation detecting elements having a different position in the slice direction.

17. A radiation detecting apparatus according to claim 13, wherein each of the radiation absorption members is a columnar member with a slice direction as its axial direction.

18. A radiation detecting apparatus according to claim 17, wherein the radiation absorption members have at least one of a circular and an ellipsoidal columnar-axis section.

19. A radiation detecting apparatus according to claim 17, wherein the radiation absorption members have columnar-axis sections that change in thickness along the radial direction from the second focal point.

20. A radiation focal-point movement detecting method comprising:

providing a radiation source configured to emit radiation to a target for imaging from a first focal point corresponding to a radiation focal point;

providing a plurality of radiation detecting elements disposed opposite to the radiation source and arranged in a channel direction;

providing a plurality of collimator plates along the channel direction on detection surface sides of the radiation detecting elements so as to separate the radiation detecting elements in the channel direction;

providing radiation absorption members at surfaces of at least one first collimator plate located on a first end side of the collimator plates and at least one second collimator plate located on a second end side of the collimator plates such that radiation shielding effects of the first and second collimator plates become substantially equivalent when the surfaces of the first and second collimator plates are located along a radial direction from a second focal point different from the first focal point; and detecting a movement of the first focal point, based on outputs of each of the radiation detecting elements separated by the first collimator plates and each of the radiation detecting elements separated by the second collimator plates.

* * * * *